US007064132B2

(12) United States Patent
Mautone

(10) Patent No.: US 7,064,132 B2
(45) Date of Patent: *Jun. 20, 2006

(54) COMPOSITION AND METHOD FOR TREATMENT OF OTITIS EXTERNAL

(75) Inventor: Alan J. Mautone, Morristown, NJ (US)

(73) Assignee: Scientific Development and Research, Inc., Belleville, NJ (US)

( * ) Notice: Subject to any disclaimer, the term of this patent is extended or adjusted under 35 U.S.C. 154(b) by 520 days.

This patent is subject to a terminal disclaimer.

(21) Appl. No.: 10/011,626

(22) Filed: Dec. 11, 2001

(65) Prior Publication Data

US 2002/0076383 A1   Jun. 20, 2002

Related U.S. Application Data

(63) Continuation-in-part of application No. 09/639,730, filed on Aug. 16, 2000, now Pat. No. 6,521,213, which is a continuation-in-part of application No. 09/450,884, filed on Nov. 28, 1999, now Pat. No. 6,156,294.

(51) Int. Cl.
*A61K 31/47* (2006.01)

(52) U.S. Cl. .................. 514/310; 514/307; 514/299; 514/279; 514/277; 514/183; 128/200.14

(58) Field of Classification Search ........... 128/200.23; 424/45; 514/951, 956, 958
See application file for complete search history.

(56) References Cited

U.S. PATENT DOCUMENTS

| | | | |
|---|---|---|---|
| 5,141,674 A | 8/1992 | Leigh | |
| 5,401,741 A | 3/1995 | Sato et al. | |
| 5,679,665 A | 10/1997 | Bergamin et al. | |
| 5,843,930 A | 12/1998 | Purwan et al. | |
| 5,888,505 A | 3/1999 | Allen | |
| 5,954,682 A | 9/1999 | Petrus | |
| 5,965,549 A | 10/1999 | Purwar et al. | |
| 6,040,463 A | 3/2000 | Balkovec et al. | |
| 6,093,417 A | 7/2000 | Petrus | |
| 6,156,294 A | 12/2000 | Mautone | |
| 6,521,213 B1 * | 2/2003 | Mautone ................ | 424/45 |

FOREIGN PATENT DOCUMENTS

WO   WO97/29738   8/1997

* cited by examiner

Primary Examiner—Christopher S. F. Low
Assistant Examiner—Michel Graffeo
(74) Attorney, Agent, or Firm—Richard L. Strauss, Esq.

(57) ABSTRACT

A compound, process and method for increasing external auditory canal patency while simultaneously preventing the occurrence of otitis externa is disclosed wherein an aerosolized mixture of lipid crystals comprised of a mixture of one or more lipids surfactants and one or more spreading agents selected from the group consisting of sterols, lipids, fatty acids, cholesteryl esters, phospholipids, carbohydrates, nucleic acids and proteins, in powder form, and one or more fluorocarbon propellants is administered directly to the external auditory canal. Upon administration, the propellant(s) are evaporated from the mixture and the lipid crystals are deposited upon an air/liquid interface resident upon epithelial tissue lining the external auditory canal. Upon contact of said lipid crystals with the epithelial lining, an amorphous spread film is formed thereupon so as to form a barrier against exogenous water while simultaneously and substantially decreasing the surface tension of said lining so as to increase the patency thereof. In a second preferred embodiment, a therapeutically active agent effective in the treatment of otitis externa is added to the mixture of lipid crystals and upon administration of said aerosol mixture, the amorphous spread film formed thereby carries said therapeutically active agent throughout the epithelium of the outer ear canal so as to improve the patency thereof by both reducing surface tension of said epithelial lining and by efficiently treating the inflammatory process. In an alternate preferred embodiment, the afore-mentioned reduction of surface tension and delivery of therapeutically active agents is provided by a mixture of lipid crystals comprised of surfactant(s), therapeutically active agents and a propellant in which such other components are not soluble. In an alternate preferred embodiment, the afore-mentioned reduction of surface tension and delivery of therapeutically active agents is provided by a mixture of lipid crystals comprised of surfactant(s), therapeutically active agents and a propellant in which such other components are not soluble.

130 Claims, No Drawings

COMPOSITION AND METHOD FOR TREATMENT OF OTITIS EXTERNAL

This is a continuation-in-part of U.S. patent application Ser. No. 09/639,730 filed on Aug. 16, 2000 which, now U.S. Pat. No. 6,521,213 in turn, is a continuation-in-part of U.S. patent application Ser. No. 09/450,884 filed on Nov. 28, 1999 and issued as U.S. Pat. No. 6,156,294 on Dec. 5, 2000.

FIELD OF INVENTION

The present invention relates to the field of pharmacological compositions and methods of utilizing such compositions to both treat and prevent the occurrence of otitis externa. More specifically, the present invention relates to a means of forming a barrier upon the epithelial lining of the outer ear canal so as to prevent the alkalization thereof or the introduction of bacteria therewithin while also providing a means of distributing and delivering therapeutically active agents, effective in the treatment of otitis externa, to the epithelial lining of said canal.

BACKGROUND OF THE INVENTION

Pathological conditions can arise from, and can cause changes in surface tension values of air/liquid interfaces resident upon tissue surfaces, especially epithelial surface tissues, of and within various organs of mammalian anatomy. The naturally occurring "surfactant system" secreted upon the epithelial lining of the lung which is deficient in cases of R.D.S. is known to be comprised of a complex mixture of lipids, proteins and carbohydrates (as described in: Surfactants and the Lining of the Lung, The John Hopkinds University Press, Baltimore, 1988).

The prime function of the surfactant system is to stabilize the alveoli and associated small airways against collapse by decreasing the surface tension at the air/liquid interface. It is now believed that the action of the phospholipid component of the surfactant system is the principal source of the powerful surface tension reduction effect of the naturally occurring surfactant system of the lung. More specifically, it is known that the fully saturated diacylphospholipids, principally dipalmitoyl phosphatidylcholine (DPPC), provide liquid balance and anti-collapse properties to the lung's epithelial lining and alveoli. In addition to DPPC, spreading agents, also found within the naturally occurring surfactant system, assist DPPC in rapidly forming a uniform spread film on the air/liquid surfaces of the lung. Such spreading agents include cholesteryl esters such as, for example, cholesteryl palmitate (CP); phospholipids such as, for example, diacylophosphatidylglycerols (PG), diacylphosphatidylethanolamines (PE), diacylphosphatidylserines (PS), diacylphosphatidylinositols (PI), sphingomelin (Sph) and Cardiolipin (Card) and virtually and other phospholipid, and the lysophospholipids; or any of the plasmalogens, dialklylphospholipids, phosphonolipids; carbohydrates and proteins, such as, for example, albumin, pulmonary surfactant proteins A, B, C and D. The naturally occurring surfactant system is further described in U.S. Pat. No. 5,306, 483.

DPPC has been administered to infants with respiratory distress syndrome as a therapeutic measure in order to restore deficient or low levels of natural surfactant. For this purpose, DPPC has been administered by means of an aqueous aerosol generator (utilized with an incubator in which the infant resided during treatment). Endotracheal administration has also been utilized. DPPC therapy has been typified as utilizing natural surfactants (harvested from porcine or bovine lungs), or artificial, commercially synthesized compounds.

It has also heretofore been disclosed to utilize therapeutic agents, in combination with surfactant/spreading agents to effectively administer drug therapy uniformly throughout the epithelial lining of the lung. U.S. Pat. No. 5,306,483 (the "'483 patent") discloses a process to prepare lipid crystalline figures in fluorocarbon propellants for the delivery of therapeutically active substances which form amorphous fluids on delivery at the air/liquid interface of the lung and which can be utilized as an effective drug delivery system. More specifically, said patent discloses a process comprising (a) preparing a mixture of one or more lipids of the group of phospholipids known as phosphatidylcholines and one or more spreading agents, in powder form and a therapeutically active substance and one or more fluorocarbon propellants, said lipids, spreading agents and therapeutically active substances being insoluble in the propellants; and (b) evaporating the propellants from the mixture. The '483 patent teaches the combination of dipalmitoyl phosphatidylcholine (DPPC) or any of the other fully saturated Acyl chain phospholipids, 80.0 to 99.5% by weight, and other spreading agents, for example, phospholipids such as, but not limited to PG, PE, PS, PI, lysophospholipids, plasmalogens, dialkylphospholipids, diether phosphonolipids, Cardiolipin, sphingomyelin, 0.5 to 20.0% weight; neutral lipids like cholesteryl esters such as, but no limited to, cholesteryl palmitate, cholesteryl oleate, cholesteryl stearate, 0.5 to 10% by weight, carbohydrates, such as, but not limited to, glucose, fructose, galactose, pneumogalactan, dextrose, 0.5 to 10% by weight; and proteins such as, but not limited to albumin, pulmonary surfactant specific proteins A, B, C, and D 0.5 to 10% by weight, yielding lipid-crystalline structures in fluorocarbon (both chloro- and hydrofluorocarbon) propellants in which therapeutically active agents, drugs and other materials can be carried into the lungs after release from and through metered dose nebulizer. The spreading agents referred to in the '483 patent are compounds such as the above-described phospholipids, lysophospholipids, plasmalogens, dialklyphospholipids, phosphonolipids, carbohydrates and proteins. The function of the spreading agent is to assist DPPC, or other phospholipids such as, for example, DPPG, in rapidly adsorbing and forming a spread film upon the air/liquid surfaces of the lungs. In addition, the '483 patent also discloses a process for preparing such lipid crystalline figures in fluorocarbon propellants without a therapeutically active substance for use as a tear (as for the eye).

The outer air canal, or, as it is also known, the external auditory canal, is lined with epithelium. It is susceptible to the same type of skin diseases as effect skin in other parts of the mammalian anatomy including, for example, eczema and psoriasis. Glands within the canal secrete a waxy exudate known as cerumen which aids in trapping air born debris as well as acidifying the epithelial surface. Such acidification, in turn, minimizes the overgrowth of bacteria. However, upon exposure to copious amounts of exogenous water such as, for instance, during swimming, the epithelial lining may become more alkaline, leading to an increased growth and over-growth in bacteria. Strains of Staphylococcus, Streptococcus and Psuedomonas species often capitalize on such alkaline conditions leading to infection and the resultant inflammatory response characteristic of infective otitis externa—immune mediated swelling, redness, heat and pain, often associated with a discharge which contains white blood cells—. Discomfort caused by this condition ranges from a slight itch to severe pain. Temporary deafness may also result as swelling and discharge physically closes off the ear canal and prevents conduction of ambient sound to the ear drum. In addition to bacteria, fungal and viral organisms are also causative of infective otitis externa. Non-microbial antigenic material is causative of another form otitis externa—specifically, allergic otitis externa—.

The cerumen exudate, normally secreted upon the epithelial tissue lining the external auditory canal, imparts a particularly high surface tension thereto which is useful in preventing foreign matter from reaching the tympanic membrane and effecting the middle and inner ear. Inflammatory by-products, discussed in greater detail below, can further increase such surface tension. Increased surface tension is an important factor in both the symptoms and treatment of otitis externa. The epithelial wall lining the outer ear canal exhibits greater than usual surface tension during otitis externa due to the secretion thereupon of proteinaceous inflammatory waste material resulting from the lysis, phagocytosis and necrosis of antigenic material. In addition, cerumen production increases in response to inflammation of the epithelial lining of the external auditory canal. This material is highly viscous in nature. Furthermore, and also as a result of the inflammatory process, the epithelium may become extremely swollen thereby causing proximal and/or opposing walls of the auditory canal to come into close approximation of one another. As such exudate laden walls come into close proximity, the high surface tension thereof may cause the adhesion of such opposing and/or proximal walls so as to completely close off the external auditory canal.

The closure of the external auditory canal is highly problematic in that both the treatment as well as the symptoms of otitis externa are negatively effected since such closure: i. blocks the transmission of sound to the middle ear; ii may result in painful increased pressure against the ear drum; and iii. inhibits and resists the application of medicine—through the external auditory meatus—to the effected tissues. In addition, and even in the absence of canal closure, the afore-mentioned increased surface tensions resident upon the epithelial lining of the outer ear canal, tends to inhibit uniform and/or effective application of therapeutic agents effective in the treatment of the inflammatory condition as well as such agents effective in treatment of the underlying causative antigenic triggers.

As discussed in greater detail below, antigenic material can induce, through the inflammatory response, a marked increase in cerumen secretion from the epithelial lining of the outer ear canal. In addition, the inflammatory response to increased quantities of antigenic material quite often results in increased permeability of capillaries located close to the epithelial lining. Such increased permeability results in a localized edema or swelling of the epithelial lining of the external ear canal discussed above. Such edema is the direct result, in part, of various components of blood seeping into the interstitial epithelial spaces including migration of antibody laden white cells therein where pmns may complex with the antigenic trigger of the inflammatory reaction. A substantial quantity of the resulting waste material is often excreted onto the epithelial lining of the cerumen covered external auditory canal wherein said material, highly viscous in nature, greatly elevates there surface tension of the epithelial lining.

The localized edema—observed as substantial swelling of the epithelial walls of the outer ear canal—tends to narrow this conduit between the lateral terminus of the external auditory meatus and the tympanic membrane. At the same time, the proteinaceous remnants of inflammatory phagocytosis, lysis and enzymatic destruction, discussed above, combine with the increased quantity of cerumen to form a coating upon the epithelial lining of the outer ear canal with substantially increased surface tension values.

For example, during the course of a common example of otitis externa, often referred to as "swimmer's ear," the out ear canal is filled with water. The effect of the water upon the normally acidic epithelial lining of the external auditory canal, is to overcome the bacteriostatic low ph conditions provided by healthy cerumen production, and cause alkalinization. Rising ph level of the outer canal allow bacteria, such as, for example species of staphylococcus, streptococcus and pseudomonas to multiply, overwhelm, and invade the epithelium. Water exposure may also act as a vector in introducing toxic and/or irritating chemicals into the ear canal wherein such chemicals act as antigens and/or break down the integrity of the epithelial lining of the external canal and allow bacterial, fungal and other microbial agents into the epithelial tissue.

Within the epithelium, the antigenic proteins of such bacteria—or in other cases, fungal, viral or other antigenic material—may come into contact with macrophages present in such tissue. Such macrophages may induce an initial immune response by presenting such antigenic material to T-lymphocytes such as, for example, a CD4+ T lymphocyte. Upon such presentation, CD4+ lymphocytes respond, in part, by releasing a multitude of interleukins and cytokines which, in turn, promote the production of increased quantities of cerumen. In addition, presentation of antigen to lymphocyte leads to a cascade of inflammatory activity wherein pmns, with activated antibody, leach out of capillaries which have been made permeable thereto by histamine, into the epithelium wherein they complex with antigen for phagcytotic, lytic and macrophagic activities. The release of arachidonic acid from such activated mast cells, macrophages and pmns may lead to, for example, the production of luekotrienes. Luekotrienes, have inflammatory effects similar to histamine. However, luekotrienes effect such chemotaxis and enhanced mucous production to a far greater degree than histamine.

Two inflammatory effects, localized edema and increased exudate surface tension act, in concert, to promote and enable the above-described attraction and adhesion of proximal epithelial surfaces to one another leading to increased blockage of the outer ear canal. However, it is the high surface tension properties of the secretions that allow and promote proximal inflamed tissues of the outer ear to remain adherent upon each other. In addition, prior to the afore-mentioned inflammatory response, it is often the effect of water: i. causing alkalinization induced bacterial overgrowth—, ii. acting as a vector for chemical toxins/irritants, or iii. directly effect in interrupting the epithelial barrier of the outer ear canal that allows antigen contact to initiate the above-described inflammatory cascade that comprises otitis externa.

In the past, otitis externa has been treated with the topical application of therapeutic agents demonstrating antimicrobial activity as well as anti-inflammatory action. Broad spectrum topically effective antibiotic otic suspensions containing antibacterial agents such as, for example, neomycin sulfate, colistin sulfate, polymyxin b, or combinations thereof, all broad spectrum in effect, have been utilized to destroy causative bacteria. Anti-mycotic topically acting agents such as, for example, nystatin and clotrimazole have been employed to destroy underlying fungal disease. In addition, the anti-viral agent acyclovir has been utilized to treat viral based otits externa including herpes zoster.

Anti-inflammatory agents, often included in the above-identified topically acting suspensions, have been employed to control the inflammatory process of otis externa including, for example, hydrocortisone, hydrocortisone acetate and dexamethasone sodium phosphate. Most often, the above-described therapeutically active agents are utilized in combination to treat both the causative, triggering disorder, e.g. bacterial infection, as well as the inflammatory process itself. They are also most often utilized in drop form for topical administration to the effected ear. In order to enhance a more uniform delivery of such medications to the epithelial lining of the outer ear canal, wicks, comprised of absorbent material such as, for example, cotton, are utilized to draw the suspensions into the ear canal for as complete an administration as possible. However, due to the above-described exudate present in purulent forms of otitis externa, and the cerumen present in virtually all inflammatory conditions, high surface tension within the canal is resistant of uniform distribution of any of said therapeutic agents throughout the outer ear canal.

What is needed is a composition, process and method for providing a barrier upon the epithelial lining of the external auditory canal so as to protect same from the above-described deleterious effects of water and water-born toxins, irritants and antigenic materials. If would be further advantageous if such a composition, process and method was provided so as to decrease the high surface tensions associated with otitis externa so as to promote external auditory canal patency. It would be still further advantageous if a composition and method were provided for delivering therapeutically active agents, effective in the treatment of otitis externa, throughout the epithelial lining of the outer ear while simultaneously reducing the surface tension thereof.

SUMMARY OF THE INVENTION

Now, in accordance with the present invention, a composition, process and method of preventing otitis externa is provided wherein a mixture of aerosolized lipid crystals are administered to the epithelial lining of the external auditory canal whereupon said mixture of crystals forms, on contact, a liquid barrier so as to prevent contact of said epithelial lining with exogenous fluids while simultaneously reducing the surface tension of the air/liquid interface resident thereupon.

In a first preferred embodiment of the present invention, a mixture of one or more lipid surfactants and one or more spreading agents selected from the group consisting of sterols, lipids, fatty acids, cholesteryl esters, phospholipids, carbohydrates, and proteins, all in powder form, and one or more propellants prepared. The propellant is selected to be one in which the one or more lipid surfactants and one or more spreading agents are not soluble so as to enable, in part, the formation of the below-described lipid crystals. For example, fluorocarbon propellants may be advantageously selected. The lipids and the spreading agents are likewise advantageously selected to be insoluble in the propellants.

The lipid surfactants utilized in practicing the present invention are selected to be present in said mixture in an amount sufficient to effectively reduce the surface tension of the liquid/air interface of the epithelial lining of the outer ear canal to which they are applied, while the spreading agents are selected to be present in an amount sufficient to effectively distribute the lipid surfactants upon said interface. The term, "effectively reduce surface tension" as utilized throughout this application and in the claims, refers to that weight percentage range of lipid surfactant which, when present in said mixture of lipid crystals, provides a clinically significant decrease in the surface tension of the air/liquid interface resident upon the epithelium lining of the external auditory canal surface tension so as, for example, to enable evacuation of fluids held or "locked" in the canal due to elevated surface tensions therein and/or allow separation of proximal walls of the external auditory canal also due to such elevated surface tension values.

The term, "effectively distribute the lipids upon said surface" refers to that weight percentage range of spreading agent that is required in order to provide adequate spreading and distribution of the lipids upon the interface resident upon the epithelial lining of the external auditory canal so as to form, in conjunction with the lipid surfactant, an amorphous spread film thereupon and thereby facilitate the aforementioned reduction of surface tension provided by the surfactant.

It has been found that the above-described clinically significant decrease in surface tension of, and effective distribution of lipids upon the epithelial lining of the external auditory canal can be effected by a mixture comprised of from about 99.99 to about 30 weight percent lipid surfactant and from about 70 to about 0.01 spreading agent. Increased effectiveness is provided by a preferred mixture comprised of from about 99.99 to about 50 weight percent lipid surfactant and from about 50 to about 0.01 weight percent spreading agent, both based on total weight of the mixture. However, it is still further preferred that the lipid surfactants utilized in practicing the method of the present invention are present in an amount of about 80 to 99.5 percent by weight and the spreading agents are present in an amount of about 0.5 to about 20 percent by weight, both based upon the total weight of the mixture. Combination of the one or more lipids, one or more spreading agents and one or more propellants results in the formation of aerosolized lipid crystals as described in more detail, below. A metered dose of the mixture of lipid crystals is then administered, via and aerosol dispenser, to the external auditory of a mammal upon which the present method is practiced. An otic administration adaptor may be advantageously selected for such administration.

Upon administration, the propellant(s) are evaporated from an aerosolized mixture of lipid crystals which are then deposited upon the air/liquid interface resident upon the epithelial lining of the external auditory canal whereupon said lipid crystals form an amorphous spread film thereupon so as to effectively decrease the surface tension thereof as well as to form a barrier against exogenous fluids such as, for example, water.

The lipid crystals deposited upon the epithelial surfaces lining the external auditory canal and the air/liquid interface thereupon is comprised of one or more lipids which are advantageously selected to demonstrate powerful surfactant activity. In addition, the spreading agent combined therewith provide thorough distribution, throughout the external auditory canal, of the surfactant over and upon the air/liquid surface resident upon said lining. In turn, the decrease in surface tension afforded thereby tends to separate proximal and opposing epithelial walls of the external auditory canal adherent, one upon the other, so as to increase patency of said conduit and promote sound conduction therethrough when such walls are, prior to such administration, in such contact. In addition, said decrease in surface tension also minimizes and, in some instances, releases fluids locked within the canal due to high surface tension therewithin which might otherwise also serve to occlude, or partially occlude the external auditory canal. Administration of the aerosolized lipid crystals through the external auditory meatus results in deposition of said crystals upon the epithelial lining of the external auditory canal without need for the use of conduction devices such as, for example, wicks.

In a second preferred embodiment of the present invention, a method of administering therapeutically active agents effective in the treatment of otitis externa—including both agents effective in treatment of inflammation as well as those agents effective in the treatment of the agents causative thereof—directly to the effected epithelial lining—as well as a process for preparing otitis externa medicaments is disclosed. In the method of the second embodiment of the present invention, a mixture of one or more lipids, one or more spreading agents, one or more therapeutically active agent(s), effective in the treatment of otitis externa, and/or the underlying cause thereof, and one or more propellants—in which said lipid surfactant, spreading agent and therapeutically active agents are not soluble—is prepared. The one or more lipids and spreading agents are advantageously selected from the group consisting of sterols, lipids, fatty acids, cholesteryl esters, phospholipids, carbohydrates and proteins. The one or more lipids, spreading agents, and therapeutically active agent(s) are advantageously selected to be in powder form. In addition, the propellants are selected so that the lipids, spreading agents and therapeutic agents are insoluble therein. As all embodiments of the present invention, the lipid surfactants utilized in practicing the method of the second preferred embodiment of the present invention are selected to be present in an amount sufficient to effectively reduce the surface tension of the liquid/air interface of the epithelial lining to which they are applied, while the spreading agents are present in an amount sufficient to effectively distribute the lipids and forms an amorphous spread film upon said surface.

The above-described clinically significant decrease in external auditory canal surface tension, formation of an amorphous spread film and delivery of therapeutically active agent can be effected by a mixture comprised of from about 99.99 to about 30 weight percent lipid surfactant and from about 70 to about 0.01 spreading agent. However, it is preferred, and increased effectiveness is provided by a mixture comprised of from about 99.99 to about 50 weight percent lipid surfactant and from about 50 to about 0.01 weight percent spreading agent, both based on total weight of the mixture. However, it is still further preferred that in practicing the method of the second embodiment of the present invention, the lipid surfactants are present in an amount of about 80 to 99.5 percent by weight and the spreading agents are present in an amount of about 0.5 to about 20 percent by weight, both based upon the total weight of said mixture. The mixture resulting from the combination of lipid surfactant(s) spreading agent(s) and therapeutically active agent(s) and propellant forms lipid crystals which act as carriers for said therapeutically active agent. A metered dose of the mixture of aerosolized lipid crystals is then administered directly into the external auditory canal of a mammal upon which the method is practiced. A suitable bottle equipped with a metered dose valve and otic administration adaptor is advantageously utilized for this purpose.

Upon administration of the lipid crystal mixture, the propellants carry the lipid crystals in combination with therapeutically active agent(s) effective in the treatment of inflammation as well as those agents effective in the treatment of the underlying causes thereof directly to and upon the epithelial lining of the external auditory canal. The lipid crystals and therapeutically active agent(s) are then deposited upon said epithelial tissue lining whereupon the mixture forms an amorphous spread film effectively carrying said therapeutically active agent effective in the treatment of the inflammation characteristic of otitis externa and/or the underlying cause thereof, therethrough and thereupon.

During administration of the lipid crystal mixture, the propellants carry the lipid crystals in combination with therapeutically active agent(s) effective in the treatment of inflammation as well as those agents effective in the treatment of the underlying causes thereof directly to, and upon, the epithelial lining of the external auditory canal. The lipid crystals and therapeutically active agent(s) are then deposited upon said epithelial tissue lining whereupon the mixture forms an amorphous spread film effectively carrying said therapeutically active agent effective in the treatment of the inflammation characteristic of otitis externa and/or the underlying cause thereof, therethrough and thereupon.

As stated in further detail below, the therapeutically active agent is advantageously selected to be effective in the treatment of otitis externa as well as agents effective in the treatment of the underlying causes thereof provoking said immune responses leading to the above-described inflammatory responses. For example, such agents may be selected to be effective in the treatment of mycotic, viral or bacterial infections, (as well as combinations thereof) underlying and causative of said inflammatory reactions. Therefore, the second preferred method of the present invention provides a method of administering therapeutically active agents directly to the epithelial lining of the external auditory canal wherein said therapeutically active agents provide effective treatment for the subject inflammatory condition such as, for example edema—as well as the underlying causes thereof—while, simultaneously, the mixture of lipid crystals act to directly and effectively decrease the surface tension of cerumen and, especially in instances of purulent otitis externa, the viscous mucous exudate thereupon.

In a first alternative embodiment of the present invention, a method of administering therapeutically active agents effective in the treatment of otitis externa directly to the epithelial lining of the external auditory canal—including both agents effective in treatment of inflammation as well as those agents effective in the treatment of the agents causative thereof—while simultaneously decreasing the surface tension of an air/liquid interface resident thereupon is disclosed. Also disclosed is a process for preparing an otitis externa medicament to effect the afore-mentioned functions.

In practicing the method and process of the first alternate embodiment of the present invention, a mixture of one or more lipid surfactants, one or more therapeutically active agent(s), effective in the treatment of otitis externa, and/or the underlying cause thereof, and one or more propellants—in which said lipid surfactant and therapeutically active agents are not soluble—is prepared. The lipid surfactant is selected from the group consisting of sterols, lipids, fatty acids, cholesteryl esters, phospholipids, carbohydrates and proteins. The therapeutic agent may be selected from any of the afore or below-mentioned therapeutically active agents so as to provide desired therapeutic effects (regarding treatment of inflammatory conditions and the causative agents thereof). In such embodiments the mixture of lipids is comprised of a lipid surfactant and a therapeutic agent and the lipid surfactant and therapeutic agent are selected to be present in the same weight ratios as those described above and below in regards to those embodiments incorporating surfactant/spreading agent components—the therapeutic agent being present in the same respective weight percentage range as the spreading agent in such embodiments. For example, an effective result may be provided by a mixture comprised of from about 99.99 to about 30 weight percent lipid surfactant and from about 70 to about 0.01 therapeutic agent. Increased effectiveness is provided by a preferred mixture comprised of from about 99.99 to about 50 weight percent lipid surfactant and from about 50 to about 0.01 weight percent therapeutically active, both based on total weight of the mixture. However, it is still further preferred said mixture may be comprised of from about 80 to about 99.5 weight percent lipid surfactant and from about 20 to about 0.5 weight percent therapeutically active agent, based upon total weight of said mixture.

In practicing the first alternative embodiment, the therapeutically active agent may be selected as a pharmacologic agent which, in addition, is also selected from the group consisting of sterols, lipids, fatty acids, cholesteryl esters, phospholipids, carbohydrates and proteins. In such embodiments, the therapeutically active agent acts in accordance with its own pharmacologic function, as well as providing spreading agent function.

As described above, the therapeutic agent is selected to be present within the above-described weight ranges and in an amount sufficient to treat the afore-mentioned inflammatory condition and/or causative agents. The remainder of the mixture is comprised of one or more of the above-described lipid surfactants which act to reduce the surface tension of the liquid/air interface of the epithelial lining to which the mixture of lipid crystals is applied, while the therapeutically active agent provides treatment of the inflammatory condition effecting the external auditory canal, and/or the causative agents thereof. Upon evaporation of the propellant, an aerosolized mixture of lipid crystals is formed.

Upon administration of the mixture of lipid crystals and therapeutic agent to the external auditory canal via, for example, a metered dose bottle, the lipid crystal come into contact, and form an amorphous spread film upon the external auditory canal. The surfactant spread film reduces the surface tension of the canal while simultaneously delivering the therapeutic agent thereto.

In some instances, more than one such agent may be carried by means of the lipid crystals to the external auditory canal. Such agents are contemplated to be antibiotics, antiviral agents, anti-inflammatory agents (steroid and nonsteroid) anti-histamines and decongestants as well as combinations thereof. Such agents are also contemplated to include gene therapy modalities including, for example, nucelic acids and vectors thereof.

The lipid surfactants utilized in practicing the method of the present invention may be advantageously selected to be phospholipids, neutral lipids or mixtures thereof. The phospholipids utilized may be further advantageously selected to be any phospholipid of the class known as phosphatidlycholine including any fully saturated diacyl phosphatidlycholine including 1,2 dipalmitoyl phosphatidylcholine (DPPC); a diacylphosphatidylglycerol; a diacylphosphatidylethanolamine; a diacylphosphatidylserine; a diacylphosphatidylinositol; sphingomyelin, Cardiolipin, lysophospholipid; a plasmalogen; a diether phosphonolipid; or a dialklyphospholipid.

The lipids utilized in practicing the method and process of the present invention may also be advantageously selected to be either plant or animal sterols. For example, cholesterol, cholecalciferol and ergosterol may be selected. In addition fatty acids, such as, for example, palmitic acid and oleic acid may also be selected.

The cholesteryl esters utilized in practicing the method and process of the present invention may be advantageously selected to be, for example, cholesteryl palmitate, cholesteryl oleate or cholesteryl stearate. Carbohydrates utilized in the present invention may be advantageously selected to be, for example, glucose, fructose, galactose, pneumogalactan, or dextrose. Proteins especially suited and advantageously selected for use in the present invention include albumin, pulmonary surfactant specific proteins A or B or C or D, their synthetic analogs, and mixtures thereof.

The propellants may be advantageously selected to be a fluorocarbon such as, for example, chlorofluorocarbon propellants, hydrofluorocarbons or mixtures thereof. In addition, the present invention contemplates carbon dioxide as a suitable propellant. The present invention contemplates the use of carbon dioxide as a propellant as a suitable propellant. It is also contemplated that the present invention may incorporate and select any pharmaceutical grade, hypoallergenic propellant in which the other components of the mixture are not soluble—the propellant, lipids, spreading agents and therapeutically active agents must be selected so none of the afore-mentioned surfactants, spreading agents or therapeutically active agents are soluble, and thus dissolved, within the propellant. The propellant is thus selected in order to enable the formation of the aerosolized mixture of lipid crystals, discussed below. The mixture is advantageously prepared to yield crystalline forms that demonstrate a particle size equal to or less than 16 microns in diameter. The diminutive nature of the crystalline particles is, as discussed in detail below, highly advantageous in enabling dispersion and application of the aerosolized mixture.

DETAILED DESCRIPTION OF THE INVENTION

Throughout this specification and claims, the phrase "therapeutically active agent" includes any substance which is capable of altering a biologic, physiologic and/or immunologic function, in nature or degree and includes those substances generally referred to as pharmacologic agents and drugs, including gene therapy agents and the vectors thereof, in order to provide treatment of the symptoms or underlying causes of the subject inflammation; the term propellant includes all those non-toxic as well as hypoallergenic propellants in which the afore-mentioned surfactants, spreading agents and therapeutic agents are not soluble such as, for example, "fluorocarbons," and carbon dioxide. The term "flurocarbons" includes the class of both chlorofluorocarbons and hydrofluorocarbons; the term lipids includes the class of phospholipids including, but not limited to PC, PG, PE, PI and Cardiolipin; and the phrase "spreading agent(s)" refer to and includes PG, PE, PS, PI, Sph., Card., lysophospholipids, plasmalogens, dialkylphospholipids, and all others in the class phospholipid as well as cholesteryl esters (like CP), proteins, and carbohydrates.

Throughout this specification and claims, the phrase "spreading agent(s)" refers to compounds, as listed above, which assist the one or more lipid such as, for example, DPPC, in rapidly adsorbing and forming an amorphous spread film on air/liquid interfaces such as that found upon the epithelial lined lumen of the external auditory canal. In addition, the compounds referred to as "spreading agent(s)", together with the one or more lipids, are responsible for achieving and maintaining biophysical properties including, but not limited to, reduction of intermolecular attractive forces, surface tension, and the resultant attractive forces generated thereby, that tend to cause opposed surfaces, such as proximal and opposing epithelial lined walls of the external auditory canal, to adhere to each other.

A major lipid component utilized in practicing a preferred embodiment of the present invention may advantageously be selected to be phospholipid 1,2 dipalmitoyl, phosphatidlycholine (DPPC). DPPC is the most surface active of the phospholipids or any of the subclass of fully saturated acyl chain phospholipids. That is to say that DPPC, in combination with any spreading agent(s) disclosed herein, has a maximum effect in reducing surface tension at an air/liquid interface.

Another, minor lipid component that also acts as a spreading agent for the major component is advantageously selected to be diacylphosphatidylglycerol (PG). The number of carbon atoms in the acyl chains R and R', (see PG formula below) can vary between 8 and 22 and may or may not be fully saturated. DPPC and PG can be synthesized. However, since DPPC and PG are the main phospholipid constituents of cells, they are also readily extractable from such cells by non-polar solvents, i.e., chloroform, ether, acetone. DPPC's structural formula is:

$$\begin{array}{c} O \\ \| \\ CH_3(CH_2)_{14}C-O-CH_2 \\ CH_3(CH_2)_{14}C-O-CH \quad O \\ \| \\ O \quad H_2C-O-P-O-CH_2CH_2N-(CH_3)_3 \\ \| \\ O \end{array}$$

and PG's structural formula is:

$$\begin{array}{c} O \quad OH \quad OH \\ \| \quad | \quad | \\ CH_2-CH-CH_2-O-P-O-CH_2-C-CH_2 \\ | \quad | \quad | \quad | \\ O=C \quad C=O \quad OH \quad H \\ | \quad | \\ R \quad R' \end{array}$$

Phospholipids such as DPPC and CP may be obtained commercially, in a highly purified form from Fluka Chemical Co. of Ronkonkoma, N.Y.; Sigma Chemical CO. of St. Louis Mo.; and Avanti Polar Lipids of Birmingham, Ala. and Primedica of Cambridge, Mass.

DPPC and PG are preferred component(s) which may be advantageously utilized in the present inventions methods for administering therapeutically active agents to the external auditory canal. In addition, these lipids increase the patency of the auditory canal by direct action of their surfactant qualities. The constituents may be selected to be present in the composition over a fairly wide range of from 99.99 to about 30 weight percent DPPC and from about 70 to about 0.01 PG based upon total weight of the mixture. Increased effectiveness is provided by a preferred mixture comprised of from about 99.99 to about 50 weight percent DPPC and from about 50 to about 0.01 weight percent PG, both based on total weight of the mixture. However, it is still further preferred that weight percentages of from about 80% to about 99.5% DPPC and 20% to 0.5% PG be selected.

Throughout this disclosure and within the claims, the terms "increasing the patency of the external auditory canal", "reducing obstruction of the external auditory canal", and "reduction of resistance to sound conduction", all refer to the opening, and elimination of blockage of the external auditory canal so as to form a patent conduit between the external auditory meatus and the tympanic membrane. The resistance referred to results from: reduction of the volume, partial obstruction, or complete occlusion of the external auditory canal due to swelling of the epithelial walls thereof as the result of inflammation; reduction of the volume, partial obstruction or complete obstruction of said air ways and air spaces due to the accumulation of increased amounts of cerumen secreted thereupon; and reduction of the volume, partial obstruction or complete obstruction of said outer air canal due to the collection of fluids therewithin—including fluids containing the waste products of the immune response or exogenous water—.

In those embodiments of the present invention wherein the aerosolized mixture of lipid crystals does not include, or act as a carrier for, a therapeutically active agent(s), the above-described reduction in obstruction of the external auditory canal is brought about by the separation of proximal and or opposing epithelial surfaces lining the canal and collection of fluids there between by means of decreasing the surface tension thereupon. The terms "proximal epithelial surfaces lining the external auditory canal" and "proximal epithelial surfaces lining the external auditory canal" and "opposing epithelial walls" as utilized throughout this specification and throughout the claims, refers to portions of the epithelial surface lining the outer auditory canal that, due to close proximity and/or opposition to each other, may come into contact as the result of, for example, epithelial or sub-epithelial edema, excess surface secretion of cerumen, inflammatory waste products or a combination thereof; high surface tension or any combination thereof.

In those instances of the present invention wherein an anti-inflammatory is the therapeutically active agent, proximal walls of epithelial lining of the outer ear canal that are adherent to each other are separated and opened by means of both lipid crystal mediated reduction of surface tension and, upon action of said anti-inflammatory, reduction of edema, reduction of cerumen, and decrease in the viscous nature thereof.

Another lipid that can be utilized in practicing the methods of the present invention is cholesteryl palmitate(CP), which also serves as a spreading agent. This cholesteryl ester is a neutral lipid which belongs to a class of organic compounds that are also cell constituents and are extractable by non-polar solvents such as chloroform, methanol, ether, etc. The structural formula of CP is:

$$\text{[cholesteryl palmitate structure]} \quad O=C-(CH_2)_{14}-CH_3$$

CP may be obtained commercially in a highly purified form from Fluka Chemical Co. and Sigma Chemical Co and Primedica. The CP component constitutes a minor portion of the composition. As is true with all spreading agents utilized in practicing the present invention CP is selected to be present in a weight percentage sufficient so as to enable effective spread and distribution of the lipid upon the mucosal surfaces. The constituents may be selected to be present in the composition over a fairly wide range of from 99.99 to about 30 weight percent DPPC and from about 70 to about 0.01 CP based upon total weight of the mixture. Increased effectiveness is provided by a preferred mixture comprised of from about 99.99 to about 50 weight percent DPPC and from about 50 to about 0.01 weight percent CP, both based on total weight of the mixture. However it is further preferred that the CP component be selected to be present in an amount ranging from about 0.5% to 20% by weight and DPPC be selected to be present from about 99.5% to about 80%, based upon the total weight of the mixture.

The term "therapeutically active agents effective in the treatment of otitis externa" as utilized in and throughout this specification and claims, refers to those drugs effective in direct treatment of the above-described inflammatory response, as well as those drugs effective in the treatment of the underlying or precipitating cause of such inflammation. In the case of infective otitis externa, a therapeutically active agent may be selected for its particular effectiveness against viral, protozoic, bacterial, fungal and/or parasitic organisms. In cases of allergic otitis externa, such therapeutic effective agents may be selected for direct effect upon inflammation as there is no precipitating organism responsible for said condition. Therefore, the present invention contemplates embodiments which include as a therapeutic agent, singly or in combination: drugs effective in the direct treatment of inflammation such as, for example, corticosteroids including, for example, hydrocortisone, hydrocortisone acetate and dexamethasone sodium phosphate, betamethasone, betamethasone dipropionate and betamethasone valerate as well as all other effective formulations. It is also contemplated that embodiments of the present invention include, as a therapeutically active agent, anti-viral agents such as, for example zovirax; antibiotics including, for example, neomycin sulfate, colistin sulfate, polymyxin b, and anti-mycotic preparations such as nystatin and clotrimazole. It is further contemplated that certain embodiments of the present invention include combinations of anti-inflammatory agents and anti-microbial agents, the inclusion of a single or multiple antibiotic being determined by the sensitivity of an identified a causative underlying micro organism, as determined by culture and sensitivity studies.

The term "therapeutically active agent" also refers to gene therapy agents.

Such gene therapy agents, as the term is used herein, refers to a biochemical substance—as well as vectors thereof—selected from the group including, but not limited to, proteins, peptides or amino acids; nucleic acids such as DNA, including full length genes or fragments thereof derived from genomic, cDNA, or artificial coding sequences, gene regulatory elements, RNA including mRNA, tRNA, ribosomal RNA, ribozymes and anitsense RNA, oligonucleotides, oligoribonucleotides, deoxyribonucleotides and ribonucleotides as such agents may exist as isolated and purified compounds or in unpurified mixtures, such as tissue, cell or cell lysate. In addition, such agents may be naturally occurring, synthetic, or a mixture thereof. The term "all of their effective formulations" as used throughout this specification and in the claims refers to those specific species of a particular therapeutic agent effective in the treatment of the above-described inflammation and/or underlying causative agent.

The combination of lipid component(s) and spreading agent component(s) disclosed herein, may be referred to, collectively, as the "carrier" when said combination is mixed with a therapeutically active agent so as to act as a carrier therefore. When practicing the method of the present invention wherein therapeutically active agents are administered directly to the epithelial lining of the external auditory canal, it is preferred that carrier, the mixture of one or more lipids and one or more spreading agents, be comprised of a mixture of DPPC and CP in a 200:1 ratio (by weight). However, it has been found that a ratio range of from 5:1 to 300:1 (DPPC/CP) will also produce an effective carrier for this particular embodiment. If, for example, the therapeutic agent is selected to be betamethasone, the weight ratio of betamethasone to carrier (DPPC/CP) is advantageously selected to be 1 microgram betamethasone to 5 milligrams carrier. However, it has been found that a weight ratio range of 0.5 to 1000 micrograms betamethasone/5 milligrams carrier yields an effective and functional mixture.

As mentioned above, in certain preferred embodiments of the present invention, the therapeutically active agent may also act as the spreading agent component. In such instances, the therapeutically active agent is selected from the group consisting of sterols, lipids, fatty acids, cholesteryl esters, phospholipids, carbohydrates and proteins. In such instances, the surfactant component/therapeutically active agent are selected to be present in the same respective weight ratio ranges as discussed above in regards to surfactant/spreading agent.

When practicing the method of the present invention wherein the therapeutically active agent is selected to be hydrocortisone acetate it is preferred to select the weight ratio of hydrocortisone to carrier to be 1.0 milligram/4.0 milligrams.

However, it has also been found that a weight ratio range of from 0.005 to 1.5 milligrams (hydrocortisone): 4.995 to 3.5 milligrams carrier, respectively, forms an effective mixture and functional mixture. The term "effective and functional mixture" as utilized throughout this application and in the claims refers to the effectiveness of the mixture of lipid crystals in combination with said therapeutically active agent resulting from the combinations disclosed herein in: (a) reaching the target tissue of the epithelium of the external auditory canal; (b) reducing the surface tension thereupon; and (c) delivering a dose of therapeutic agent directly to and effectively spreading the surfactant and therapeutically active agent throughout the external auditory canal so as to effectively bring symptomatic relief and/or resolution of the afore-mentioned pathological conditions underlying otitis externa as well as acting, by means of said lipid crystals, to open and increase the patency of said conduit by reduction of surface tension and elimination of pooled fluids therewithin.

When practicing the method of the present invention wherein the therapeutically active agent is selected to be the antibiotic neomycin sulphate, the ratio of neomycin to carrier may be advantageously selected to be 0.4 mg antibiotic to 4.6 mg carrier (DPPC/CP) by weight. However, a weight range of from 0.1 to 1 mg neomycin:from 4.9 to 4.0 mg carrier, respectively, has been found to be fully effective in practicing the present method.

Fluorocarbon propellants are utilized in practicing the method of the present invention, namely: trichlorodifluoromethane, dichlorodifluoromethane, and tetrafluoromethane or mixtures thereof, which are commercially available from Union Carbide Corp., Danbury, Conn. and Armstrong Laboratories, West Roxbury Mass. are advantageously selected for formation of the lipid crystalline figures of the present invention. The fluorocarbon propellants may be advantageously selected to be present over a range of 2 to 30 times the amount, by weight, of lipid, but components of lipid and propellants both are needed in order to obtain the required lipid crystalline figures.

In practicing the methods of the present invention wherein therapeutically effective agents are administered directly to the epithelial lining of the external auditory canal, DPPC is advantageously selected as the major lipid component since the amphoteric nature of this phospholipid allows the molecule to act as a carrier for any drug or therapeutic agent. However, the presence of a charge on other lipid components (a negative charge on PG, for example) would alter and further improve the carrying capacity of the lipid crystals for a particular therapeutic agent.

Because of the highly amphoteric nature of the carrier utilized herein, the use of any presently known and available, as well as anti-viral, antibiotic or gene therapy agent developed in the future capable of providing effective treatment of infections of the external auditory canal and tympanic membrane are contemplated and fully functional with the methods and compositions herein.

EXAMPLE 1

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. All purchased materials were checked for purity by standard chromatographic analysis. The hydrocortisone acetate utilized in this example was also purchased from Sigma Chemical. The DPPC and CP were then mixed in the dry powder form in a weight ratio of 200:1 (DPPC:CP). To 4 milligrams of the resultant carrier, 1 milligram of hydrocortisone acetate was added in order to yield a weight ratio of 4:1 (carrier: hydrocortisone acetate). Then 5 grams of this mixture was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with an administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: hydrocortisone acetate aerosolized mixture. However, metered dose valves having a greater dosing range are also contemplated and can be utilized in other embodiments of the present invention.

EXAMPLE II

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The neomycin sulphate utilized in this example can be purchased from Parke-Davis division of Warner Lambert, Morris Plains, N.J. All purchased materials were checked for purity by standard chromatographic analysis. The DPPC and CP were then mixed in the dry powder form in a weight ratio of 200:1 (DPPC:CP). Thereafter, to 4.6 milligrams of the resultant carrier, 0.4 milligrams of neomycin sulphate was added so as to yield an approximate 11.5:1 weight ratio of carrier to neomycin sulphate . Then 5 grams of the resultant mixture (DPPC/CP/phenylephrine) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were immersed in a water bath to test for leaks and then fitted with an administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: neomycin sulphate aerosolized mixture. However, metered dose valves having a greater dosing range are also contemplated and can be advantageously utilized in practicing the methods of the present invention.

EXAMPLE III

Chromatographically pure DPPC and CP (99% pure) were obtained from Avanti Polar Lipids Co. of Birmingham, Ala. and Sigma Chemical Co. of St. Louis, Mo.

DPPC and CP were mixed in a weight ratio of 200:1 (DPPC:CP). Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with an otic adapter. The suspension was homogenous. After standing at room temperature for about three days, a pellicle forms on top of the propellants but was easily re-suspended by gentle shaking. The size of the metering valve can be varied to deliver from 1 mg up to 5.4 mg of the DPPC:CP aerosolized mixture.

The afore-described Examples "I" and "II" are specific embodiments of the aerosolized drug delivery system utilized in practicing the method of the present invention. Each of the afore-mentioned Examples "I" and "II" are administered by releasing a metered dose of the mixtures, by means of an otic administration adaptor, directly to and throughout the external auditory meatus. The aerosolized mixture, propelled by the above-described propellants, is then effectively deposited upon the air/liquid interface resident upon the epithelial lining of the external auditory canal. When the crystalline lipid figures come in contact with the epithelial surface lining, an amorphous spread film layer forms upon the air/liquid interface resident thereupon. Upon such contact, said mixture of lipid crystals by means of the afore-mentioned surfactant properties, lowers the surface tension of said air/liquid interface so as to allow the afore-mentioned opening of the external auditory canal and elimination of pooled liquid obstructions which may be present thereon.

In the above-described Example "I", wherein the therapeutically active agent is the anti-inflammatory hydrocortisone acetate, the agent acts directly upon the inflammatory process occurring within the epithelium of the external auditory canal, reducing the production of the afore-mentioned excess cerumen and viscous inflammatory secretions while also decreasing tissue edema. Both excess secretions and edema act to partially obstruct, or, in some instances, totally occlude the outer ear canal. Thus, therapeutic agents of anti-inflammatory activity increase auditory canal patency by increasing conduit volume. However, in addition to such action of anti-inflammatory agents, the DPPC and/or DPPC/PG lipids of the present invention act independently of selected therapeutic agent(s) in promoting the opening of the external auditory canal by reduction of the surface tension of the epithelial lining thereof—by reducing the intermolecular and surface charges found at the air/interface of the viscous secretion covered lumen—. Thus, DPPC and/or DPPC/PG lipids of the present invention are able to increase the patency of the external auditory canal independent of the action of any therapeutic agent carried thereby.

The present invention also contemplates the use of antibiotics such as, for example, neomycin sulphate (Example "II"), nystatin b and colistin sulphate as well as any other antibiotic agent effective in the treatment of the underlying bacterial infection. Also, it is contemplated that both antimycotic and anti-viral agents are advantageously employed for treatment of those instances of infective otits externa wherein a fungal or viral infection is the causative factor. In such embodiments, the DPPC and/or DPPC/PG act to introduce such drugs into the external auditory epithelium in the same manner as described immediately above in regards to anti-inflammatory agents. Such anti-biotic, anti-viral and anti mycotic agents act indirectly upon the inflammatory process provoked by the presence of antigenic microbial proteins by acting to reduce or eliminate the presence thereof. As the antigenic challenge of such microbes is reduced by the action of such therapeutic agents, the degree and intensity of inflammation—edema and excess cerumen—is reduced. However, while DPPC and DPPC/PG aerosolized mixtures act as carriers for such drugs, they also continue to provide the independent and more expeditiously effect auditory canal patency discussed above by effecting a decrease in surface tension of the air/liquid interface resident thereupon—on contact—. Therefore, in instances in which the method of the present invention is utilized to treat an underlying microbial infection of the external auditory canal, direct application of antibiotic therapy to the target tissues is accomplished, leading to diminished microbial activity or death. Such anti-microbial effect indirectly reduces outer auditory canal obstruction caused by inflammatory by reducing and/or eliminating the presence of such antigenic proteins.

In Example "III", above, preparation of an aerosolized mixture of lipid crystals for use in practicing the method of the present invention is disclosed that is advantageously formulated for forming a barrier against exogenous water contacting the epithelial lining of the external ear duct as well as increasing the patency thereof without the use of a therapeutically active agent. In practicing the second preferred embodiment of the present invention, the aerosolized mixture, propelled by the above-described propellants, is deposited upon the air/liquid interface resident upon the epithelial lining of the outer ear canal. Upon contact of the crystalline lipid figures with the air/liquid interface, an amorphous spread film layer is formed thereupon, effectively spreading throughout the eternal auditory canal. Upon contact with the air/liquid interface, the increased surface tensions thereof—associated with inflammation and resultant increased cerumen and exudate discussed in great detail above—is substantially reduced. The reduction of said surface tension effects an opening of the outer ear canal by releasing adherent or partially adherent proximal and/or opposing epithelial surfaces, lining said conduit—from adhesion, one to another, as well as reducing pooled fluids blocking or partially blocking said outer ear canal. In this example, no therapeutically active agent is included in the aerosolized mixture or contemplated in this embodiment. Increased patency and release of fluids is provided by means of interaction of the surfactant/spreading agent combination alone. In many instances, especially in the absence of underlying infection, such as, for example, allergic otitis externa, embodiments of the present invention not incorporating therapeutically active agents may be preferred so as to control the effects of such inflammation while minimizing systemic effects inherent in the use of Structural Characteristics Particle Size and Gross Configuration Particle size of the aerosolized crystals produced and utilized in practicing the present invention is, as discussed below, important to effective administration. The size (diameter) of the lipid crystals were therefore determined utilizing in a cascade impactor. Flow through the impactor was adjusted to be substantially identical to the flow from a nebulizer utilized in practicing the disclosed method. All of the lipid crystals were found to have a diameter equal to or less than 16 microns. The diameter of about 95 percent of the particles were found to be equal to or less than 4 microns in diameter. Of the particles found to be 4 microns or less, half were, in fact, 1 micron in diameter. The mean diameter demonstrated by the lipid crystals utilized in the method of the present invention was 1.75+/−0.25 microns.

Micronization may be advantageously utilized in order to insure reduced particle size. Therefore, the methods of the present invention also contemplate the use of a micronization mill such as, for example, the "DYNO" mill, type KDL, manufactured by Glen Mills Inc., of New Jersey in the preparation of the aerosolized mixture. For example, approximately 13.33 grams of CP and 83 grams of DPPC powder were weighed and transferred to a bead mill within the milling chamber of a DYNO mill (having about 480 cc of glass beads). The chamber was then sealed. Thereafter, 1 liter of HFC-134a was added and the system chilled to about −10° C. at a pressure of approximately 65 psi. Milling was achieved in about 1 hour. Thereafter, the resultant slurry was utilized to fill 15 mil epoxy phenolic lined aluminum cans (Safet Embamet, St. Florantine, France), fitted with Valois metering valves (DFI/ACT/kematal, Valois, Le Neuborg, France with Micron-4 acuators (also Valois). A laser particle sizer, model 2600c, Malvern Instruments, Inc., was thereafter utilized to size the resultant particles as shown in Table "1", below. This data indicates that approximately 90% of the particles emitted fro the valve and actuator system are under 7 μm or less in diameter. The mean diameter (arithmetic mean) is approximately 5 μm and the mass median aerodynamic diameter (MMAD) is about 3.4 μm with a geometric standard deviation (GSD) of about 0.5. Particle size results in physically unstable dispersions should change dramatically over a few days of undisturbed storage.

TABLE 1

Particle Size Summary

| Day Number | 90 Percentile | 50 Percentile | % ≦10 μm | MMAD | GSD |
|---|---|---|---|---|---|
| 1 | 6.9 μm | 5.1 μm | 100 | 3.4 | 0.5 |
| 2 | 6.8 μm | 4.8 μm | 99.9 | 3.5 | 0.5 |
| 3 | 7.3 μm | 5.4 μm | 100.0 | 3.5 | 0.5 |
| 4 | 6.5 μm | 4.6 μm | 99.9 | 3.2 | 0.5 |
| 5 | 6.8 μm | 4.7 μm | 100.0 | 3.4 | 0.5 |
| Mean | 6.9 ± 0.3 μm | 4.9 ± 0.3 μm | 100.0 | 3.4 ± 0.1 | 0.5 |

Structural characteristics of the mixture of lipid crystals utilized in practicing the present invention were further assessed by capturing the aerosolized particles on standard scanning electron microscopic grids fixed to glass slides at 22° C., (dry). The lipids deposited on glass both as dry particles and as coalesced droplets. The latter evaporated immediately leaving dry lipid. The dry lipids, were fixed in osmium vapor ($O_sO_4$), coated and viewed with a scanning electron microscope. Crystalline figures about 100 angstroms thick, were grouped in clumps on the dry surface. This is a unique configuration.

Crystalline Structure

The mixture of one or more lipids, one or more spreading and one or more propellants disclosed in the present invention is especially formulated and combined to form a unique crystalline structure with physical dimensions highly advantageous to all embodiments. For this reason, the propellants must be selected so that the surfactant and spreading agents are not soluble therein. For example, the crystalline structure results in, as discussed above, a mean particle size of 1.75 microns. The minute physical dimensions of the individual nebulized particles enables the propellant utilized in practicing the present invention to easily and effectively transfer the disclosed mixture to and throughout the desired target tissue. A larger physical configurations such as, for example, a liposome, would not enable such diminutive particle size within and effective physical transport by the propellant.

Functional Properties

The aerosolized mixture of the present invention is crystalline. The crystalline nature of the mixture imparts increased efficiency of particle dispersion within the aerosol mist applied by means of a metered-dose nebulizer. Upon application, the fluorocarbon medium, either chlorofluorocarbon or hydrofluorocarbon, vaporizes rapidly and the DPPC/CP, DPPC/CP drug, DPPC/PG drug or DPPC/PG/CP drug dispersion deposits on an aqueous surface at 37° C., initially in the crystalline form, and then, instantaneously, spreads over the surface as an amorphous surface film. In embodiments wherein a therapeutic is combined with the carrier, the drug likewise is effectively spread upon the aqueous surface.

The surfactant/spreading agent functions and characteristics of the method and composition of the present invention were tested as follows. Aerosolized crystalline figures of the present invention were impacted upon a liquid surface (normal saline solution, NSS) at 37° C., 100% humidity in a surface balance resulted in a rapid spreading of a principally amorphous film that covered the entire surface (18.1 $cm^2$). Surface tension of the film was measured during expansion and compression at 37° C., 100% humidity. Film expansion to 110.4 $cm^2$ produced a surface tension of 72 dynes/cm and compression to 18.1 $cm^2$ lowered surface tension to less than 1 dyne/cm.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A method of increasing mammalian external auditory canal patency while simultaneously providing protection against the occurrence of otitis externa therewithin comprising administering a dose of a mixture of lipid crystals, as an aerosol, through an external auditory meatus of a mammal, said mixture being comprised of at least one lipid surfactant in an amount effective in lowering surface tension of an air/liquid interface resident upon epithelial tissue lining said external auditory canal, at least one spreading agent in an amount effective in distributing said surfactant upon said interface and at least one propellant in which said surfactants and spreading agents are not soluble, said lipid surfactants and said spreading agents being selected from the group consisting of lipids, sterols, fatty acids, cholesteryl esters, phospholipids, carbohydrates, and proteins, all in powder form;

whereupon when said mixture is so administered, the propellants are evaporated from said mixture as said lipid crystals come into contact with, and deposit upon the epithelial lining of the external auditory canal and form an amorphous spread film thereupon so as to reduce the surface tension thereof while also forming a barrier thereupon to exogenous fluids.

2. The method of claim 1 wherein said amount of lipid surfactant is selected to be present in an amount of from about 99.99 to about 50 weight percent and wherein said spreading agent is selected to be present in an amount of from about 50 to about 0.01 weight percent.

3. The method of claim 1 wherein said lipid surfactant is selected to be present in an amount of from about 80 to about 99.5 weight percent and wherein said spreading agent is selected to be present in an amount of from about 20 to about 0.5 weight percent.

4. The method of claim 1 wherein a metered dose inhalation device is filled with said mixture of lipid crystals and thereafter said device is utilized to administer a metered dose of said mixture by means of an otic administration adaptor.

5. The method of claim 1 wherein the sterols are cholesterol, ergosterol, cholecalciferol or mixtures thereof.

6. The method of claim 1 wherein the fatty acids are palmitic acid, oleic acid or mixtures thereof.

7. The method of claim 1 wherein the lipids are phospholipids, neutral lipids or mixtures thereof.

8. The method of claim 7 wherein the phospholipids are any of a class known as phosphatidylcholines.

9. The method of claim 8 wherein the phosphatidylcholine is any fully saturated diacyl phosphatidylcholine.

10. The method of claim 9 wherein the fully saturated diacyl phosphatidylcholine is 1,2 dipalmitoyl phosphatidylcholine.

11. The method of claim 7 wherein the phospholipid is a diacylphosphatidylglycerol, diacylphosphatidylethanolamine, diacylphosphatidylserine, diacylphosphatidylinositol, sphingomelin, Cardiolipin, lysophospholipid, plasmalogen, diether phosphonolipid, dialkylphospholipid, or a mixture thereof.

12. The method of claim 1 wherein the carbohydrates are glucose, fructose, galactose, pneumogalactan, dextrose or mixtures thereof.

13. The method of claim 1 wherein the protein is selected from albumin and pulmonary surfactant specific proteins A or B or C or D or mixtures thereof.

14. The method of claim 1 wherein the cholesteryl ester is cholesteryl palmitate, cholesteryl oleate, cholesteryl stearate or mixtures thereof.

15. The method of claim 1 wherein the propellants are fluorocarbons.

16. The method of claim 15 wherein the fluorocarbon is a chlorofluorocarbon, hydrofluorocarbon or mixtures thereof.

17. The method of claim 1 wherein the propellant is carbon dioxide.

18. The method of claim 1 wherein the propellant is any pharmaceutical grade hypo-allergenic propellant in which neither the surfactant or spreading agent are soluble.

19. The method of claim 1 wherein 95 percent of said crystals demonstrate a particle size no greater than 4 microns in diameter.

20. A method of increasing mammalian external auditory canal patency while simultaneously administering therapeutically active agents effective in the treatment of otitis externa directly to the external auditory canal comprising administering a dose of a mixture of lipid crystals, as an aerosol, through an external auditory meatus of a mammal, said mixture being comprised of at least one lipid surfactant in an amount effective in lowering surface tension of an air/liquid interface resident upon epithelial tissue lining said external auditory canal, at least one spreading agent in an amount effective in distributing said surfactant upon said interface, at least one therapeutically active agent effective in the treatment of otitis externa and one or more propellants, said surfactants and said spreading agents being selected from the group consisting of sterols, lipids, fatty acids, cholesteryl esters, phospholipids, carbohydrates, and proteins, said surfactants, spreading agents and therapeutically active agents all being in powder form and insoluble in the propellants, whereupon when said mixture is so administered, the propellants are evaporated from said mixture as said lipid crystals come into contact with, and deposit upon the epithelial lining of the external auditory canal and form an amorphous spread film thereupon so as to reduce the surface tension thereof, deliver said therapeutically active agent thereto and form a barrier to exogenous fluids thereupon.

21. The method of claim 20 wherein said lipid surfactant is selected to be present in an amount of from about 99.99 to about 50 weight percent and wherein said spreading agent is selected to be present in an amount of from about 50 to about 0.01 weight percent.

22. The method of claim 20 wherein said lipid surfactant is selected to be present in an amount of from about 80 to about 99.5 weight percent and wherein said spreading agent is selected to be present in an amount of from about 20 to about 0.5 weight percent.

23. The method of claim 20 wherein a metered dose inhalation device is filled with said mixture of lipid crystals in combination with said therapeutically active agent and thereafter said device is utilized to administer a metered dose of said mixture by means of an otic administration adaptor.

24. The method of claim 20 wherein the sterols are cholesterol, ergosterol, cholecalciferol or mixtures thereof.

25. The method of claim 20 wherein the fatty acids are palmitic acid, oleic acid or mixtures thereof.

26. The method of claim 20 wherein the lipids are phospholipids, neutral lipids or mixtures thereof.

27. The method of claim 26 wherein the phospholipids are any of a class known as phosphatidylcholines.

28. The method of claim 27 wherein the phosphatidylcholine is any fully saturated diacyl phosphatidylcholine.

29. The method of claim 28 wherein the fully saturated diacyl phosphatidylcholine is 1,2 dipalmitoyl phosphatidylcholine.

30. The method of claim 26 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, or a mixture thereof.

31. The method of claim 20 wherein the carbohydrates are glucose, fructose, galactose, pneumogalactan, dextrose or mixtures thereof.

32. The method of claim 20 wherein the protein is selected from albumin and pulmonary surfactant specific proteins A or B or C or D or mixtures thereof.

33. The method of claim 20 wherein the cholesteryl ester is cholesteryl palmitate, cholesteryl oleate, cholesteryl stearate or mixture thereof.

34. The method of claim 20 wherein said therapeutically active agent is an anti-inflammatory, antibiotic, decongestant or gene therapy agent.

35. The method of claim 34 wherein said anti-inflammatory agent is betamethasone.

36. The method of claim 34 wherein said antibiotic is erythromycin, amoxicillin, zythromax and Augmentin.

37. The method of claim 34 wherein said decongestant is phenylephrine.

38. The method of claim 20 wherein the propellants are fluorocarbons.

39. The method of claim 38 wherein the fluorocarbon is a chlorofluorocarbon, hydrofluorocarbon or mixtures thereof.

40. The method of claim 20 wherein the propellant is carbon dioxide.

41. The method of claim 20 wherein the propellant is any pharmaceutical grade, hypo-allergenic propellant in which neither the surfactant, spreading agent or therapeutically active agent are soluble.

42. The method of claim 20 wherein 95 percent of said crystals demonstrate a particle size no greater than 4 microns in diameter. method of claim 28 wherein the lipids are phospholipids, neutral lipids or mixtures thereof.

43. A process for preparing an external auditory canal patency enhancing and protective medicament comprising:
combining at least one lipid surfactant, at least one spreading agent, and at least one propellant to form a mixture, said lipids and said spreading agents being selected from the group consisting of sterols, lipids, fatty acids, cholesteryl esters, phospholipids, carbohydrates, all in powder form, wherein said lipids and said spreading agents are insoluble in the propellants and said lipid surfactants are present in an amount effective in reducing surface tension of an air/liquid interface resident upon epithelial tissue lining the external auditory canal and said spreading agents being present in an amount effective in distributing said surfactant upon said interface when said propellants are evaporated from said mixture to form an aerosolized mixture of lipid crystals for use as the medicament.

44. The process of claim 43 wherein said lipid surfactant is selected to be present in an amount of from about 99.99 to about 50 weight percent and wherein said spreading agent is selected to be present in an amount of from about 50 to about 0.01 weight percent.

45. The process of claim 43 wherein said lipid surfactant is selected to be present in an amount of from about 80 to about 99.5 weight percent and wherein said spreading agent is selected to be present in an amount of from about 20 to about 0.5 weight percent.

46. The process of claim 43 further comprising bottling said mixture within a metered dose device.

47. The process of claim 43 wherein the sterols are selected to be cholesterol, ergosterol, cholecalciferol or mixtures thereof.

48. The process of claim 43 wherein the fatty acids are selected to be palmitic acid, oleic acid or mixtures thereof.

49. The process of claim 43 wherein the lipids are selected to be phospholipids, neutral lipids or mixtures thereof.

50. The process of claim 49 wherein the phospholipids are selected to be any of a class known as phosphatidylcholines.

51. The process of claim 50 wherein the phosphatidylcholine is selected to be any fully saturated diacyl phosphatidylcholine.

52. The process of claim 51 wherein the fully saturated diacyl phosphatidylcholine is selected to be 1,2 dipalmitoyl phosphatidylcholine.

53. The process of claim 49 wherein the phospholipid is selected to be a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, or a mixture thereof.

54. The process of claim 43 wherein the carbohydrates are selected to be glucose, fructose, galactose, pneumogalactan, dextrose or mixtures thereof.

55. The process of claim 43 wherein the protein is selected from albumin and pulmonary surfactant specific proteins A or B or C or D or mixtures thereof.

56. The process of claim 43 wherein the cholesteryl ester is selected to be cholesteryl palmitate, cholesteryl oleate, cholesteryl stearate or mixtures thereof.

57. The process of claim 43 wherein the propellants are selected to be fluorocarbons.

58. The process of claim 57 wherein the fluorocarbon is selected to be a chlorofluorocarbon, hydrofluorocarbon or mixtures thereof.

59. The process of claim 43 wherein the propellant is selected to be carbon dioxide.

60. The process of claim 43 wherein the propellant is selected to be any pharmaceutical grade hypo-allergenic propellant in which the at least one surfactant and spreading agent are not soluble.

61. The process of claim 43 wherein 95 percent of said crystals demonstrate a particle size no greater than 4 microns in diameter.

62. A process for preparing an otitis externa medicament comprising: combining at least one lipid surfactant, at least one spreading agent, at least one therapeutically active agents effective in the treatment of otitis externa and at least one propellants to form a mixture, said lipid surfactants and said spreading agents being selected from the group consisting of sterols, lipids, fatty acids, cholesteryl esters, phospholipids, carbohydrates, all in powder form, wherein said lipids, said spreading agents and said therapeutically active agents are insoluble in the propellants and said lipid surfactants are selected to be present in an amount effective in reducing surface tension of an air/liquid interface resident upon epithelial tissue lining the external auditory canal and said spreading agents are selected to be present in an amount effective in distributing said surfactant and therapeutically active agents upon said interface when said propellants are evaporated from said mixture to form an aerosolized mixture of lipid crystals in combination with the therapeutically active agent for use as the medicament.

63. The process of claim 62 wherein said lipid surfactant is selected to be present in an amount of from about 99.99 to about 50 weight percent and wherein said spreading agent is selected to be present in an amount of from about 50 to about 0.01 weight percent.

64. The process of claim 62 wherein said lipid surfactant is selected to be present in an amount of from about 80 to about 99.5 weight percent and wherein said spreading agent is selected to be present in an amount of from about 20 to about 0.5 weight percent.

65. The process of claim 62 further comprising bottling said mixture within a metered dose device.

66. The process of claim 62 wherein the sterols are selected to be cholesterol, ergosterol, cholecalciferol or mixtures thereof.

67. The process of claim 62 wherein the fatty acids are selected to be palmitic acid, oleic acid or mixtures thereof.

68. The process of claim 62 wherein the lipids are selected to be phospholipids, neutral lipids or mixtures thereof.

69. The process of claim 68 wherein the phospholipids are selected to be any of a class known as phosphatidylcholines.

70. The process of claim 69 wherein the phosphatidylcholine is selected to be any fully saturated diacyl phosphatidylcholine.

71. The process of claim 70 wherein the fully saturated diacyl phosphatidylcholine is selected to be 1,2 dipalmitoyl phosphatidylcholine.

72. The process of claim 68 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, or a mixture thereof.

73. The process of claim 62 wherein the carbohydrates are selected to be glucose, fructose, galactose, pneumogalactan, dextrose or mixtures thereof.

74. The process of claim 62 wherein the protein is selected from albumin and pulmonary surfactant specific proteins A or B or C or D or mixtures thereof.

75. The process of claim 62 wherein the cholesteryl ester is selected to be cholesteryl palmitate, cholesteryl oleate, cholesteryl stearate or mixtures thereof.

76. The process of claim 62 wherein said therapeutically active agent is selected to be an anti-inflammatory, antibiotic, decongestant or gene therapy agent.

77. The process of claim 76 wherein the anti-inflammatory agent is selected to be betamethasone.

78. The process of claim 76 wherein said antibiotic is selected to be erythromycin, amoxicillin, zythromax, Augmentin or mixtures thereof.

79. The process of claim 76 wherein the decongestant is selected to be phenylephrine.

80. The process of claim 62 wherein the propellants are selected to be fluorocarbons.

81. The process of claim 80 wherein the fluorocarbon is selected to be a chlorofluorocarbon, hydrofluorocarbon or mixtures thereof.

82. The process of claim 62 wherein the propellant is selected to be carbon dioxide.

83. The process of claim 62 wherein the propellant is selected to be any hypo-allergenic, pharmaceutical grade propellant in which the neither the surfactant, spreading agent or therapeutically active agent are soluble.

84. The process of claim 62 wherein 95 percent of said crystals demonstrate a particle size no greater than 4 microns in diameter.

85. A method of administering therapeutically active agents, effective in the treatment of otitis externa, directly to mammalian external auditory canal tissues while simultaneously increasing canal patency comprising administering a dose of a mixture of lipid crystals in combination with said therapeutically active agents, as an aerosolized mixture, through an external auditory meatus of a mammal, said mixture being comprised of at least one lipid surfactant in an amount effective in lowering surface tension of an air/liquid interface resident upon epithelial tissue lining said canal, at least one therapeutically active agent effective in the treatment of otitis externa and at least one propellant, said lipid surfactants being selected from the group consisting of sterols, lipids, fatty acids, cholesteryl esters, phospholipids, carbohydrates, and proteins, said surfactants and therapeutically active agents all being in powder form and insoluble in the propellants, whereupon, when said mixture of lipid crystals is so administered, said propellants evaporate from said mixture as said crystals come into contact with, and deposit upon the epithelial lining of the external auditory canal so as to reduce the surface tension thereof while distributing said therapeutically active agent within said canal to said tissues.

86. The method of claim 85 wherein said lipid surfactant is selected to be present in an amount of from about 99.99 to about 50 weight percent and wherein said therapeutically active agent is selected to be present in an amount of from about 50 to about 0.01 weight percent.

87. The method of claim 85 wherein said lipid surfactant is selected to be present in an amount of from about 80 to about 99.5 weight percent and wherein said therapeutically active agent is selected to be present in an amount of from about 20 to about 0.5 weight percent.

88. The method of claim 85 wherein a metered dose inhalation device is filled with said mixture of lipid crystals in combination with said therapeutically active agent and thereafter said device is utilized to administer a metered dose of said mixture by means of an otic administration adaptor.

89. The method of claim 85 wherein the sterols are cholesterol, ergosterol, cholecalciferol or mixtures thereof.

90. The method of claim 85 wherein the fatty acids are palmitic acid, oleic acid or mixtures thereof.

91. The method of claim 85 wherein the lipids are phospholipids, neutral lipids or mixtures thereof.

92. The method of claim 91 wherein the phospholipids are any of a class known as phosphatidylcholines.

93. The method of claim 92 wherein the phosphatidylcholine is any fully saturated diacyl phosphatidylcholine.

94. The method of claim 93 wherein the fully saturated diacyl phosphatidylcholine is 1,2 dipalmitoyl phosphatidylcholine.

95. The method of claim 91 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, or a mixture thereof.

96. The method of claim 85 wherein the carbohydrates are glucose, fructose, galactose, pneumogalactan, dextrose or mixtures thereof.

97. The method of claim 85 wherein the protein is selected from albumin and pulmonary surfactant specific proteins A or B or C or D or mixtures thereof.

98. The method of claim 85 wherein the cholesteryl ester is cholesteryl palmitate, cholesteryl oleate, cholesteryl stearate or mixture thereof.

99. The method of claim 85 wherein said therapeutically active agent is an anti-inflammatory, antibiotic, decongestant or gene therapy agent.

100. The method of claim 99 wherein said anti-inflammatory agent is betamethasone.

101. The method of claim 99 wherein said antibiotic is erythromycin, amoxicillin, zythromax and Augmentin.

102. The method of claim 99 wherein said decongestant is phenylephrine.

103. The method of claim 85 wherein the propellants are fluorocarbons.

104. The method of claim 103 wherein the fluorocarbon is a chlorofluorocarbon, hydrofluorocarbon or mixtures thereof.

105. The method of claim 85 wherein the propellant is carbon dioxide.

106. The method of claim 85 wherein the propellant is selected to be any pharmaceutical grade, hypo-allergenic propellant in which neither the at least one surfactant or therapeutically active agent are soluble.

107. The method of claim 85 wherein the therapeutic agent is selected from the group consisting of sterols, lipids, fatty acids, cholesteryl esters, phospholipids, carbohydrates, and proteins.

108. A process for preparing an otitis externa medicament comprising: combining at least one lipid surfactant, at least one therapeutically active agent effective in the treatment of otitis externa and at least one propellant to form a mixture, said lipid surfactants being selected from the group consisting of sterols, lipids, fatty acids, cholesteryl esters, phospholipids, carbohydrates, and proteins all in powder form, wherein said lipids and said therapeutically active agents are insoluble in the propellants and said lipids are selected to be present in an amount effective in lowering surface tension of an air/liquid interface resident upon epithelium lining of the external auditory canal and effective in distributing said therapeutically active agent therewithin when said propellants are evaporated to form an aerosolized mixture of lipid crystals combined with said therapeutic agents for use as the medicament.

109. The process of claim 108 wherein said lipid surfactant is selected to be present in an amount of from about 99.99 to about 50 weight percent and wherein said therapeutically active agent is selected to be present in an amount of from about 50 to about 0.01 weight percent.

110. The process of claim 108 wherein said lipid surfactant is selected to be present in an amount of from about 80 to about 99.5 weight percent and wherein said therapeutically active agent is selected to be present in an amount of from about 20 to about 0.5 weight percent.

111. The process of claim 108 further comprising bottling said mixture within a metered dose administration device.

112. The process of claim 108 wherein the sterols are cholesterol, ergosterol, cholecalciferol or mixtures thereof.

113. The process of claim 108 wherein the fatty acids are palmitic acid, oleic acid or mixtures thereof.

114. The process of claim 108 wherein the lipids are phospholipids, neutral lipids or mixtures thereof.

115. The process of claim 114 wherein the phospholipids are any of a class known as phosphatidylcholines.

116. The process of claim 115 wherein the phosphatidylcholine is any fully saturated diacyl phosphatidylcholine.

117. The process of claim 116 wherein the fully saturated diacyl phosphatidylcholine is 1,2 dipalmitoyl phosphatidylcholine.

118. The process of claim 114 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, or a mixture thereof.

119. The process of claim 108 wherein the carbohydrates are glucose, fructose, galactose, pneumogalactan, dextrose or mixtures thereof.

120. The process of claim 108 wherein the protein is selected from albumin and pulmonary surfactant specific proteins A or B or C or D or mixtures thereof.

121. The process of claim 108 wherein the cholesteryl ester is cholesteryl palmitate, cholesteryl oleate, cholesteryl stearate or mixture thereof.

122. The process of claim 108 wherein said therapeutically active agent is an anti-inflammatory, antibiotic, decongestant or gene therapy agent.

123. The process of claim 122 wherein said anti-inflammatory agent is betamethasone.

124. The process of claim 122 wherein said antibiotic is erythromycin, amoxicillin, zythromax and Augmentin.

125. The process of claim 122 wherein said decongestant is phenylephrine.

126. The process of claim 108 wherein the therapeutically active agent is selected from the group consisting of sterols, lipids, fatty acids, cholesteryl esters, phospholipids, carbohydrates, and proteins.

127. The process of claim 108 wherein the propellants are fluorocarbons.

128. The process of claim 127 wherein the fluorocarbon is a chlorofluorocarbon, hydrofluorocarbon or mixtures thereof.

129. The process of claim 108 wherein the propellant is selected to be carbon dioxide.

130. The process of claim 108 wherein the propellant is selected to be any pharmaceutical grade, hypo-allergenic propellant in which neither that at least one surfactant or therapeutic agent are soluble.

* * * * *